Figure 1:
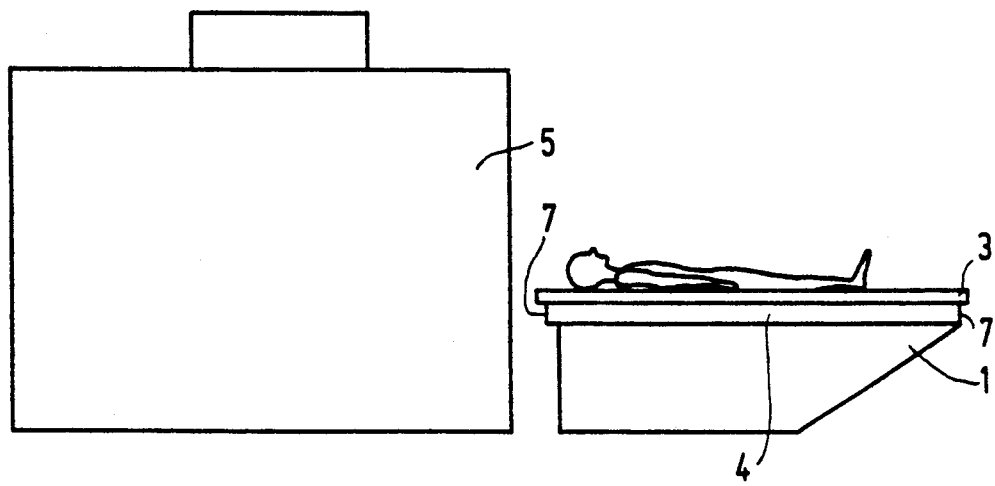

United States Patent [19]

Lammers et al.

[11] Patent Number: 5,014,968

[45] Date of Patent: May 14, 1991

[54] PATIENT POSITIONING AND TRANSPORT SYSTEM

[75] Inventors: Jan F. Lammers; Antonius J. L. M. Hoeks; Frank D. S. Kennedy Van Dam, all of Eindhoven, Netherlands

[73] Assignee: U.S. Philips Corporation, New York, N.Y.

[21] Appl. No.: 439,215

[22] Filed: Nov. 17, 1989

[30] Foreign Application Priority Data

Nov. 22, 1988 [NL] Netherlands .................. 8802874

[51] Int. Cl.⁵ .............................................. A61G 13/00
[52] U.S. Cl. .................................................. 269/322
[58] Field of Search ............... 269/322, 73; 378/177, 378/209; 108/137, 143; 5/81 B

[56] References Cited

U.S. PATENT DOCUMENTS

| | | |
|---|---|---|
| 2,526,879 | 10/1950 | Kitzaur . |
| 4,131,802 | 12/1978 | Broden et al. ............ 269/322 |
| 4,568,071 | 2/1986 | Rice ........................... 269/322 |
| 4,641,823 | 2/1987 | Bergman .................... 269/322 |
| 4,700,938 | 10/1987 | Chambron ................. 269/322 |

FOREIGN PATENT DOCUMENTS

| | | |
|---|---|---|
| 214023 | 3/1961 | Austria . |
| 2817989 | 4/1977 | Fed. Rep. of Germany ...... 269/322 |
| 1156415 | 6/1969 | United Kingdom . |

Primary Examiner—Robert C. Watson
Attorney, Agent, or Firm—William Squire

[57] ABSTRACT

A patient table has round surface edges for coupling between a troley and a patient table for the transfer of a table top from the trolley to the patient table. When the patient table is lifted by a table lifting mechanism, the table top is decoupled from the trolley after which the trolley can be decoupled from the patient table so as to be removed. The lifting construction of the patient table enables a large stroke to be made in a vertical direction without giving rise to longitudinal displacement of the table includes top. The patient table a hydraulic displacement mechanism for a longitudinal displacement of the table top; this mechanism can also be operated by hand in the case of emergencies.

18 Claims, 3 Drawing Sheets

PATIENT POSITIONING AND TRANSPORT SYSTEM

The invention relates to a patient table and positioning system for medical diagnostic purposes, comprising a patient table, a trolley comprising carrier arms and a table top which is detachably arranged on the patient table so as to enable its transfer to the trolley.

The invention also relates to a patient table, a trolley and a table top for use in such a system.

A system of the kind set forth is known from British Patent Specification No. GB 1,156,415.

This document describes a system for patient transport and positioning in which a table top which is loosely arranged on a trolley can be coupled to a patient table in a lateral direction. To this end, the table top comprises two guide faces which project along the sides and which fit in two slots of the patient table. A system comprising a table top which is detachable from the patient table is of importance for efficient use of medical diagnostic equipment utilizing the patient table. When, for example for X-ray examinations, a patient is prepared in a separate room, which preparation may include the installation of supporting or fixing elements for keeping the patient in the correct position, another patient can undergo a diagnostic examination. The detachability of the table top is also attractive from a point of view of access to the patient during the preparation preceding the examination.

A patient transport and positioning system of the kind set forth has the drawback that the coupling of the table top to the patient table necessitates exact positioning of the trolley and the table top with respect to the patient table, which implies that the guide faces and the slots must be substantially parallel before the table top is slid off the trolley. It is an intricate and time-consuming operation to maneuver the trolley, usually provided with casters, into the correct position; in the case of a not exactly horizontal position of the table top with respect to the patient table jamming may occur between the slots and the guide faces. Furthermore, in order to enable a lateral movement between the table top and the trolley it is necessary for the table top to be slidable on the carrier arms substantially without friction. However, during the transport of the trolley this has the drawback that the table top is liable to be shifted with respect to the trolley so that travel on a floor which is not exactly flat is problematic.

It is an object of the invention to provide a patient transport and positioning system in which fast and simple displacement of the table top between the patient table and the trolley is possible and in which the table top cannot slide off the trolley during transport of the trolley.

To achieve this, a patient transport and positioning system in accordance with the invention is characterized in that the side faces of the patient table can be brought into contact with guide faces of the carrier arms by displacement of the trolley in a direction parallel to the table top, the side faces being curved.

A preferred embodiment of a patient transport and positioning system in accordance with the invention is characterized in that the side faces have a common center of curvature.

Because of the curvature of the side faces which preferably have a cylindrical shape, the trolley can be simply positioned with respect to the patient table by first bringing the guide faces of the trolley into contact with the side faces of the patient table for an arbitrary position of the trolley and the patient table with respect to one another, and by subsequently rotating the trolley about the center of curvature of the side faces until the trolley is situated in a desired position adjacent the table. Thus, the problems involved in the exact positioning of the trolley with respect to the table top and the patient table before coupling the trolley to the patient table are avoided.

A preferred embodiment of a patient transport and positioning system in which the height of the patient table is adjustable in accordance with the invention is characterized in that the trolley comprises locking pawls for coupling the trolley to the patient table and for vertically coupling the table top to the trolley, which vertical coupling can be released both by placing the table top above the patient table, followed by displacement of the patient table in the vertical direction, and by displacement of buttons or grips provided on the trolley.

In order to couple the trolley to the patient table in the correct position for transferring the table top to the patient table, the guide faces are provided with locking pawls which fit in recesses in the side walls of the patient table. When the elements are suitably positioned with respect to one another, the locking pawls engage the recesses, thus fixing the trolley with respect to the patient table. For medical diagnostic examinations a displacement of the patient table in the longitudinal and/or vertical direction is often desirable. Because the table top is coupled to the trolley, preventing sliding of the table top with respect to the trolley during transport, the table top should be decoupled from the trolley before longitudinal displacement of the table top across the patient table can take place. After the table top has been transferred to the patient table, the trolley can be decoupled from the patient table by operating two grips, so that the trolley can be moved aside. Because the table top should also be detachable from the trolley without intervention of the patient table, for example for cleaning, the trolley comprises grips or buttons for decoupling the vertical coupling. Such a grip or button is user friendly because of its ease of operation and integration in the trolley.

A further embodiment of a patient transport and positioning system in which the patient table comprises a drive for longitudinal movement of the table top in accordance with the invention is characterized in that the drive comprises pulleys and a hydraulic cylinder provided with a piston whereto there are connected two piston rods which emerge from the cylinder at both sides, to each piston rod there being coupled a pulley on which a wire is guided, a pawl which fits in a recess in a lower side of the table top being connected to said wire, the pawl being movable in a longitudinal direction with a stroke which is at least equal to the stroke of the piston.

Longitudinal displacement of the table top with respect to the patient table is necessary, for example for MR imaging where the patient to be examined is arranged in a magnet. As a result of the pulley construction, a large stroke of the table top can be achieved by way of a small piston stroke. Preferably, the table top is moved across the patient table on wheels. Because of its compact construction, the drive can be simply arranged underneath the patient table. Because the cylinder volumes on both sides of the piston are the same in a central position of the piston in the cylinder, the piston can be displaced by the transfer of liquid from one cylinder volume to the other cylinder volume. As a result, the hydraulic system can be simplified and the piston stroke can be simply controlled. By connecting the cylinder volumes on both sides of the piston to a liquid duct which can be closed for example by means of a valve, the cylinder can be displaced by hand by opening the valve in the case of a fault in the hydraulic system. This is advantageous, for example for MR examinations where the table top with a patient is slid into a magnet and where the patient should be situated outside the magnet for suitable patient access.

It is to be noted that a hydraulic drive comprising a pulley construction is known per se from U.S. Pat. No. 2,526,879. However, according to this Patent Specification cassette holders are displaced instead of a table top. The cassette holders are displaced by means of a piston comprising one piston rod, so that hydraulic control of the cylinder is more difficult and manual control is not possible in the case of emergencies.

A further embodiment of a patient transport and positioning system in which the patient table comprises a lifting device in accordance with the invention is characterized in that the lifting device is capable of displacing the table top in a vertical direction, without causing a lateral displacement of the table top with respect to the patient table and/or with respect to a reference point situated outside the patient table, during this vertical displacement.

The construction of the lifting mechanism enables the patient table to be moved in a vertical direction without the table top being displaced in a horizontal direction; moreover, the lifting device is compact in its lowest position. A side elevation of the lifting device reveals an upper and a lower pivot at the left-hand side and an upper and a lower pivot at the right-hand side, halfway between the right-hand pivots there being situated a third right-hand pivot which is connected, by way of two rods of substantially equal length, to the upper and lower right-hand pivots, the left-hand upper and lower pivots being coupled by way of two substantially equally long rods and a coupling, the coupling being connected to the third right-hand pivot by way of a transverse rod. The transmission, for example two gearwheels, enables an oppositely directed rotation of the connecting rods between the left-hand pivots of the lifting device, which rotation is transmitted, via the transverse rod, to the rods which interconnect the right-hand pivots of the lifting device. This results in a uniformly distributed application of force and a forceful lifting movement. In any position of the patient table play-free loading of the patient table is possible by loading the gearwheel members with a moment, for example by means of a resilient pin.

It is to be noted that a lifting mechanism in which an oppositely directed rotation of lifting parts by coupling using gear wheel members is known per se from Austrian Patent Specification No. AT 214023. This Patent Specification describes a lifting mechanism enabling a rotation of the table top in combination with a lifting motion of the table top. As a result, contact with the floor is avoided in tilted positions of the table top. The gearwheel members merely serve to couple the direction of rotation of two rods of the lifting mechanism according to the cited Patent Specification and can be replaced, for example by a coupling belt, the position of the gearwheel members not being changed during the lifting motion. This is contrary to the gearwheel members in accordance with the invention which enable inter alia loading of the patient table, which is free from lateral play.

Figure 2A:
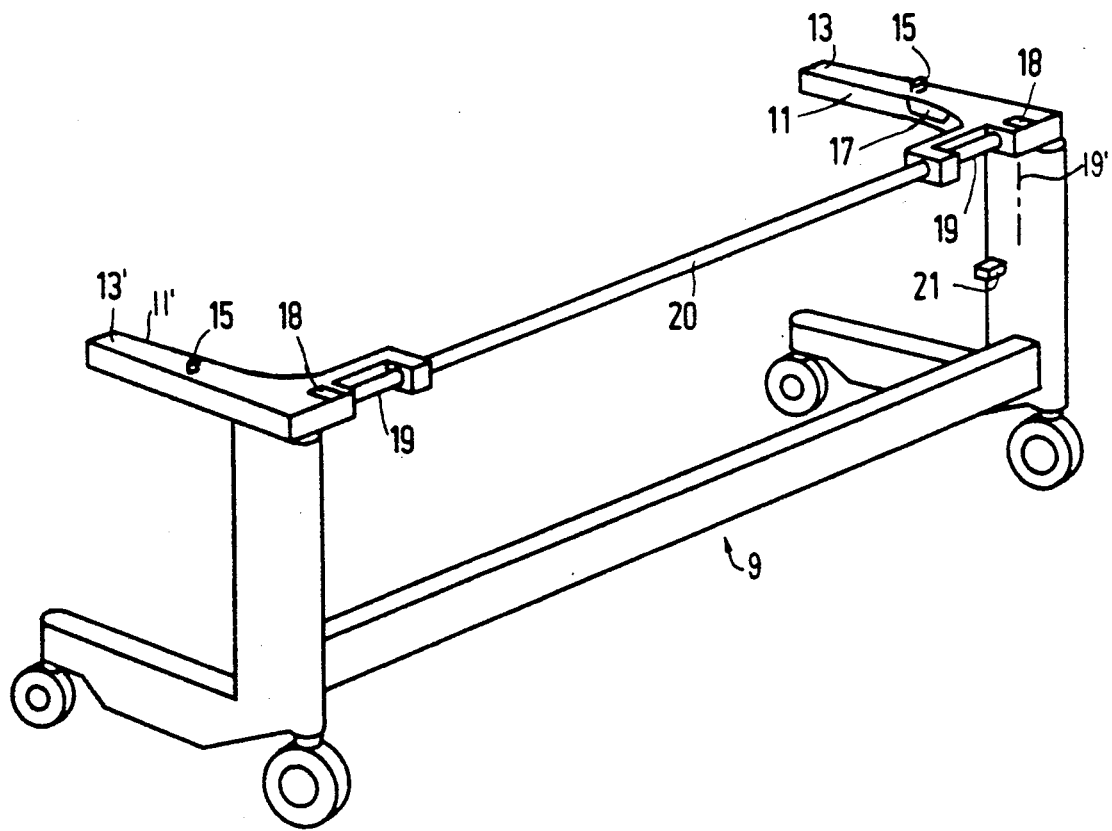
Figure 2B:
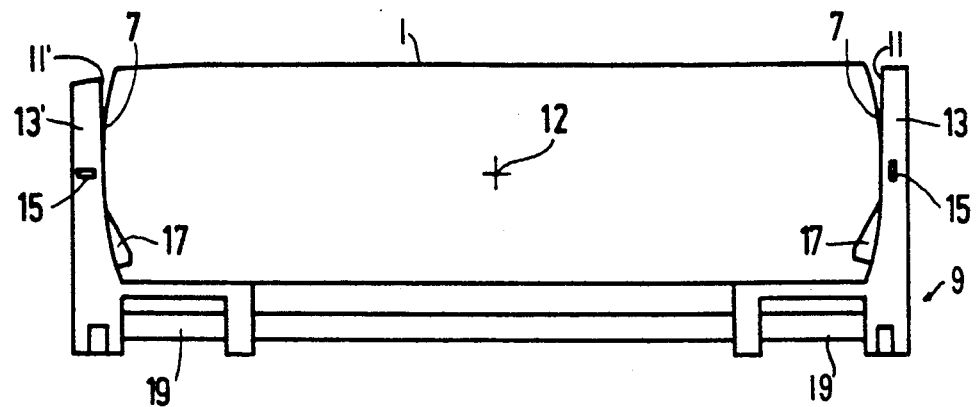
Figure 3A:
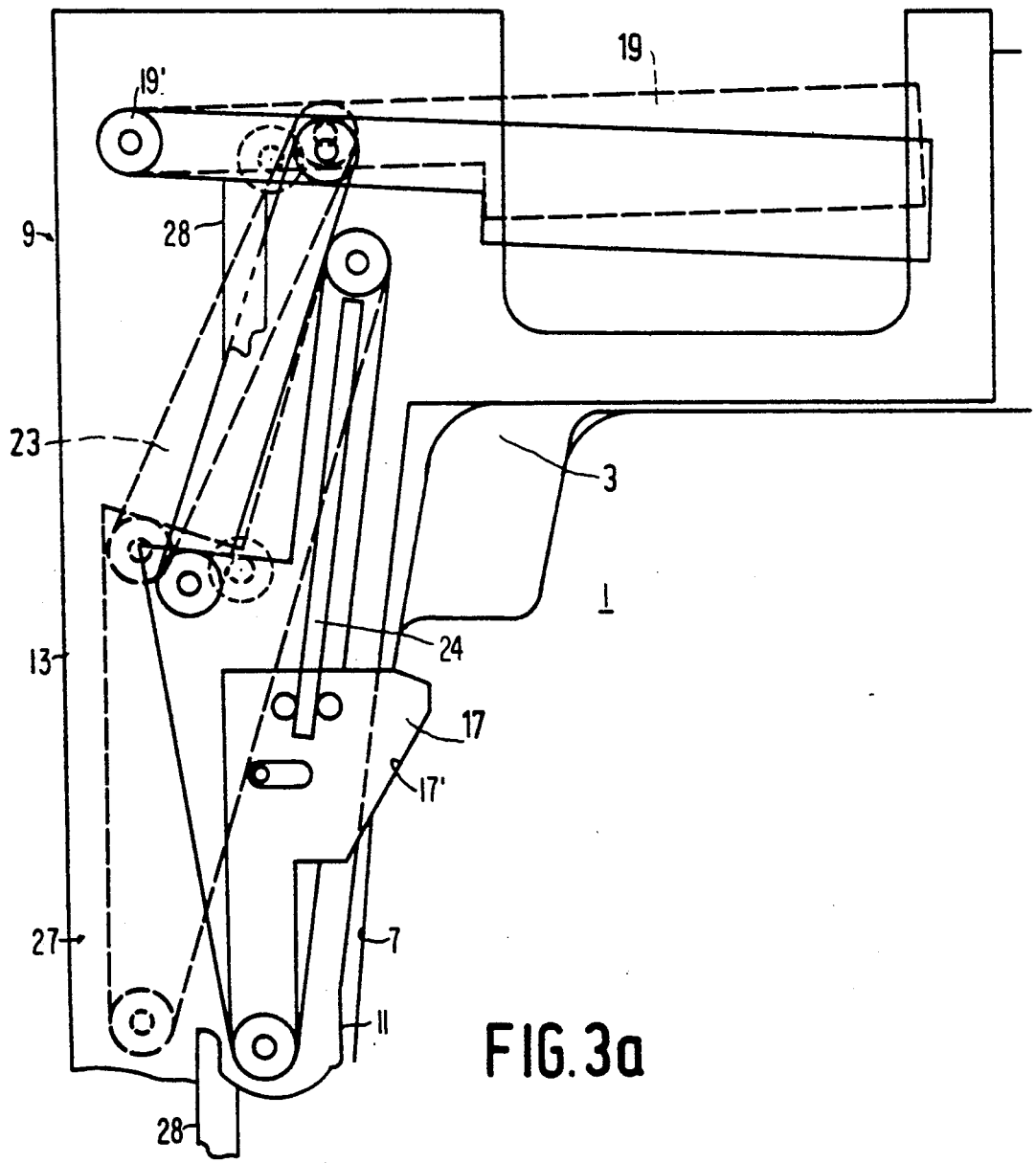
Figure 3B:
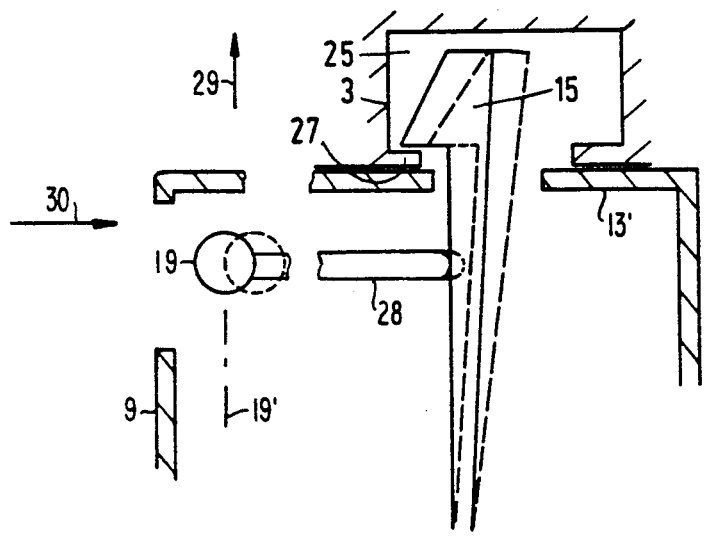
Figure 4:
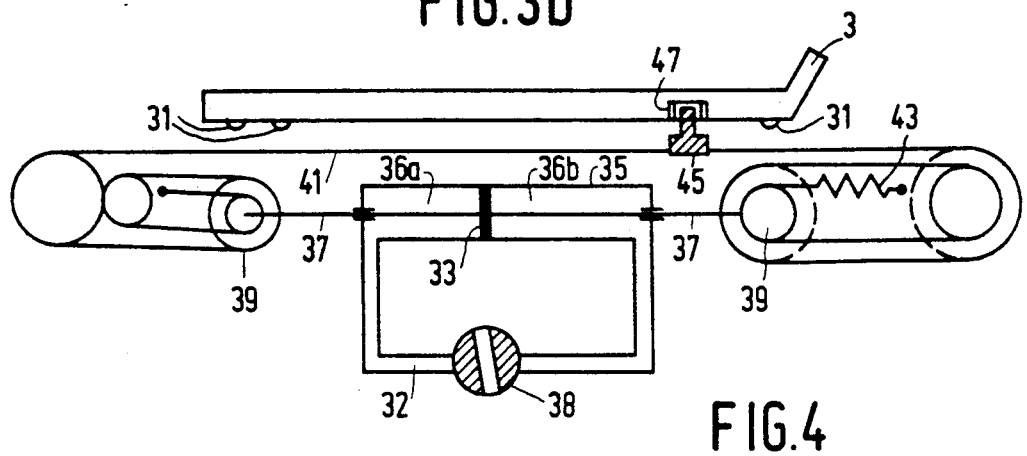
Figure 5:
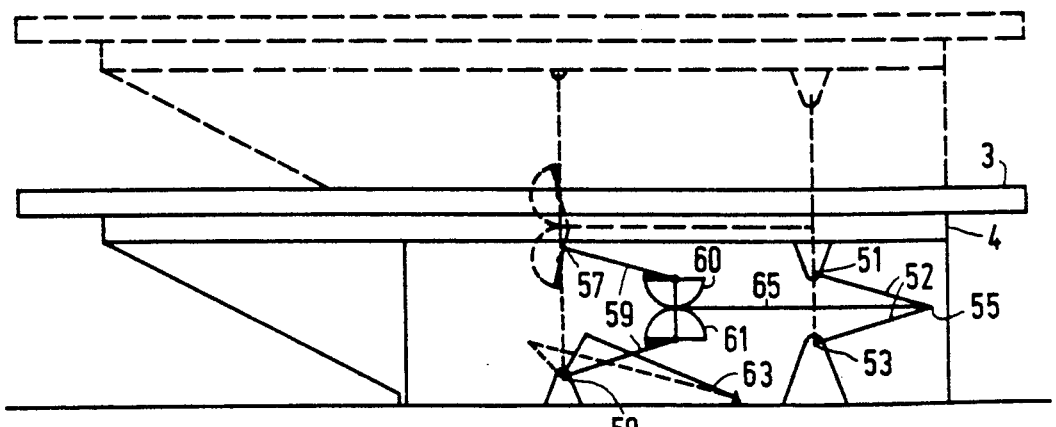

Some embodiments of a patient transport and positioning system in accordance with the invention will be described in detail hereinafter with reference to the accompanying drawing. Therein:

FIG. 1 diagrammatically shows an elevation view of an examination system including a patient table and a table top, FIG. 2a diagrammatically shows an isometric view of a trolley in accordance with one embodiment of the invention, FIG. 2b is a plan view of the trolley of FIG. 2a coupled to the patient table of FIG. 1, FIG. 3a shows a plan view of a trolley coupling of the patient table and the trolley, FIG. 3b shows a side elevation view of a vertical coupling of the table top and the trolley, FIG. 4 shows a side elevation view of a drive for displacing the table top in a longitudinal direction, and FIG. 5 shows a side elevation view of a lifting device for the patient table.

FIG. 1 shows a patient table 1, comprising a detachable table top 3 which is displaceable in a longitudinal direction on a support 4; in this case it is intended to be slid into an MR apparatus 5. For transferring the table top 3 from the patient table 1 to the trolley (not shown in the drawing), the trolley must occupy an accurately reproducible position with respect to the patient table 1. To this end, the preferably cylindrically curved side walls 7 of the patient table are brought into contact with the guide faces of the carrier arms of the trolley.

FIG. 2a shows a trolley 9 where the guide faces 11 and 11' of the respective carrier arms 13 and 13' are curved. The table top 3 (not shown in this Figure) is releasably secured to the carrier arms 13 and 13'. The table top is retained on the trolley 9 by way of a vertical latch 15 on arms 13 and 13' so that the table top cannot slide with respect to the trolley during transport. The vertical locking latch 15 on each arm is moved by rotating the respective grips 19 about vertical axis 19' or under the influence of the patient table acting on the pawl 21. By rotating the grips 19 about a vertical axis the horizontal locking pawl 17 is also withdrawn, so that the trolley can be transported away from the table.

FIG. 2b is a plan view of the trolley 9 positioned against the patient table 1. Because of the curved shape of the side walls 7 of the patient table, the trolley can be simply positioned by arranging a guide face 11 against a first side wall 7 of the patient table and by subsequently bringing the other guide face 11 into contact with the second side wall 7 by rotating the trolley about the center of curvature 12. Because of a partial curvature of the respective guide faces 11 and 11' of the carrier arms 13 and 13', the trolley can be locked to the patient table by way of the locking pawls 17 at the area of contact between the guide faces 11 and 11' and the side walls 7.

FIG. 3a shows a horizontal latching means for operating pawl 17 which engages in a recess 17' in the patient table 1. When the grip 19 is not moved, during the positioning of the guide faces 11 and 11' of the trolley 9 against the side faces 7 of the patient table 1, the pawl 17 will be pushed away against the force of a resilient member 24 until the pawl 17 enters the recess 17' in a side wall of the patient table 1. When the grip 19 is rotated about vertical axis 19', the arm 23 via connected linkage 27 pulls the pawl 17 out of the recess so that the trolley is decoupled.

FIG. 3b shows how the grip 19 can be moved about vertical axis 19' so as to push away the vertical locking latch 15, preferably made of an elastic material, such that lip 27 of recess 25 in table top 3 is released from latch 15 and the table top 3 is displaceable in the vertical direction 29. Instead of using a grip 19, the vertical coupling can also be decoupled by means of a button 18 (FIG. 2a) which disengages latch 15 from lip 27. The grip 19 is connected to a link 28. When grip 19 is rotated about axis 19', the link 28 is pushed in direction 30. The link 28 engages latch 15 and causes latch 15 to disengage from lip 27 when so pushed. As noted above, when grip 19 is so rotated, it also disengages latch 17 from the table recess 17'.

FIG. 4 shows a piston 33 which is displaceable in a cylinder 35. To both sides of the piston 33 there are connected piston rods 37 whereto pulleys 39 comprising two grooves are secured. A wire 41 is guided around the pulleys 39, one end of the wire 41 being connected to a tensioning spring member 43. To the wire 41 there is connected a pawl 45 which is displaceable in an elongated slot (not shown) in the support 4 for the patient table 1 and which engages a cavity 47 in the table top 3. When the piston 33 is displaced, the table top 3 which has wheels 31, is displaced in a longitudinal direction with a stroke which is four times larger than the stroke of the piston in the present embodiment. The pressure on the piston 3 can be delivered by one compressor which also builds up the pressure whereby the lifting of the patient table can be realised. The cylinder volumes 36a and 36b communicate via a liquid duct 32 when a valve 38 is open. When the valve 38 is open, the piston can be displaced by hand by transferring a volume of liquid from the cylinder volume 36a to the cylinder volume 36b by means (not shown).

FIG. 5 is a side elevation of a lifting device in accordance with the invention. The right-hand pivots 51 and 53 are connected to a third right-hand pivot 55 by way of two rods 52. The left-hand pivots 57 and 58 are coupled by way of two rods 59 and gears 60 and 61. Under the influence of a, for example, hydraulic drive 63, the engaging gears 60 and 61 rotate in opposite directions and force the pivot 57 upwards. The transverse rod 65 exerts a tensile force on the pivot 55, so that the pivot 51 is raised. Thus, a uniform distribution of the lifting force on the table top is obtained, and the lifting device occupies only comparatively little space in its lowest position. When the height is changed, the table top 3 is displaced only in the vertical direction, without compensation for longitudinal movement being required.

We claim:

1. A patient table and positioning system for medical diagnostic purposes comprising;
   a patient table having a table top support surface and at least one curved side wall having a plurality of spaced curved side wall portions;
   a trolley including a plurality of table top support arms each having a guide face; and
   a table top adapted to be carried on the patient table and on the support arms;
   said guide faces being spaced for receiving and guiding the curved side wall portions of the patient table therebetween so that when the trolley guide faces are brought into contact with the table side wall portions, the table top support surface is aligned relative to said support arms.

2. The system of claim 1 wherein said side wall portions have a common center of curvature.

3. The system of claim 1 wherein said patient table includes adjustment means for adjusting the height of the table top support surface, said table and trolley including locking means including locking pawls for releasably securing the trolley to the table, said table and top including aligning and securing means for releasably securing and aligning the top to the table.

4. The system as claimed in claim 1 in which the patient table includes a drive for longitudinal movement of the table top, said drive including a plurality of pulleys and a hydraulic cylinder provided with a piston whereto there are connected two piston rods which emerge from the cylinder at opposite sides, to each piston rod there being coupled a pulley on which a wire is guided, a pawl which fits in a recess in a lower side of the table top being connected to said wire, the pawl being movable in said longitudinal direction with a stroke which is at least equal to the stroke of the piston.

5. The system as claimed in claim 4 wherein the cylinder has two opposing volumes on opposite sides of the piston, said system including a duct and valve means coupled to the duct for selectively fluid coupling said two volumes.

6. The system as claimed in claim 1 in which the patient table includes a lifting device, said lifting device including means for displacing the table top in a vertical direction without causing a lateral displacement of the table top with respect to the patient table and with respect to a reference point situated outside the patient table during this vertical displacement.

7. The system as claimed in claim 6, wherein the lifting device includes spaced pairs of upper and a lower pivots at opposing sides of the device, a third pivot being situated spaced from one of said pairs of pivots and substantially equally spaced from the one pair, which third pivot is connected to the upper and lower pivots of said one pair by way of two rods, respectively, of substantially equal length, the other of said pair of upper and lower pivots being coupled by way of two substantially equal length rods and a coupling, the coupling being connected to the third pivot by a transverse rod.

8. The system as claimed in claim 7 wherein the coupling comprises two engaging gearwheel members, the centers of curvature of which are interconnected by a link which is rigidly connected to an end of the transverse rod opposite the connection to said third pivot.

9. A patient table and positioning system for a medical diagnostic system comprising:
   a patient table having a table top receiving surface and first and second spaced curved side surfaces;
   a table top for receiving a patient thereon and adapted to be releasably secured to said top receiving surface;
   a trolley including means for releasably supporting said table top thereon and having a plurality of spaced curved table receiving curved side faces for receiving said curved side surfaces therebetween, said curved table receiving surfaces defining a table receiving receptacle, and
   means secured to the trolley for releasably securing the trolley to said table and for aligning via said curved surfaces and side faces the table top carried by the trolley to the table top receiving surface.

10. The system of claim 9 wherein said table includes means for releasable securing the top thereto.

11. The system of claim 10 wherein said means for securing the top and for securing the trolley to the table include displaceable grip means which displace in a given direction and actuating means responsive to the displacement of said grip means in said given direction to release the trolley from the table and to release the top from the trolley.

12. A patient table and positioning system for medical diagnostic purposes comprising:
   a patient table having first table top support means and spaced curved side wall portions;
   a trolley having second table top support means; and
   a table top adapted to be carried by the first and second support means;
   said trolley including spaced guide faces for receiving, engaging and guiding the curved side wall portions of the patient table so that when the trolley guide faces are brought into engagement with the table curved side wall portions, the first table top support means is aligned relative to said second table top support means for transfer of the top to the table from the trolley and to the trolley from the table.

13. The system of claim 12 wherein said second support means comprises a pair of spaced table top support arms, each arm having one of said guide faces for receiving the table side wall portions therebetween.

14. The system of claim 12 wherein the trolley includes latch means for releasably securing the top to the trolley and the trolley to the table.

15. The system of claim 14 wherein said latch means includes displaceable grip means for releasing the top and for releasing the trolley in response to displacement of the grip means.

16. A trolley for use in a patient table and positioning system for medical diagnostic purposes in which a table has a first table top support means for releasably receiving a patient supporting table top, said table having spaced curved sidewall portions, said trolley comprising:
   a frame;
   wheel means for permitting the frame to be displaced over a floor; and
   second table top support means coupled to the frame for supporting said top;
   said frame including spaced guide faces for receiving, engaging and guiding the curved side wall portions of the patient table so that when the trolley guide faces are brought into engagement with the table curved side wall portions, the first table top support means is aligned relative to said second table top support means for transfer of the top to the table from the trolley and to the trolley from the table.

17. A table for use in a patient table and positioning system for medical diagnostic purposes in which a trolley has a first table top support means for releasably receiving a patient supporting table top, said trolley including spaced guide faces, said table comprising:
   a frame;
   second table top support means coupled to the frame for releasably receiving the top; and
   spaced curved side wall portions coupled to the frame dimensioned and arranged to mate with said guide faces for aligning the first table top support means relative to said second table top support means for transfer of the top to the table from the trolley and from the trolley to the table.

18. A patient table and positioning system for medical diagnostic purposes comprising:
   a patient table having first table top support means and spaced curved side wall portions;
   a trolley having second table top support means; and
   a table top adapted to be carried by the first and second support means;
   said trolley including spaced guide faces corresponding to and for receiving, engaging and guiding the corresponding curved side wall portions of the patient table so that when one of the trolley guide faces is brought into engagement with a table curved side wall portion, the other of said guide faces is aligned with its corresponding curved side wall portion for engagement therewith such that the first table top support means is aligned relative to said second table top support means for transfer of the top to the table from the trolley and to the trolley from the table.

* * * * *